United States Patent [19]

Patchett et al.

[11] 3,991,185

[45] Nov. 9, 1976

[54] METHODS FOR TREATING COCCIDIOSIS WITH EMIMYCIN AND ITS DERIVATIVES

[75] Inventors: Arthur A. Patchett, Cranford; Ching C. Wang, Watchung, both of N.J.

[73] Assignee: Merck & Co., Inc., Rahway, N.J.

[22] Filed: May 12, 1975

[21] Appl. No.: 576,942

Related U.S. Application Data

[63] Continuation-in-part of Ser. No. 449,152, March 7, 1974, abandoned.

[52] U.S. Cl. .............................. 424/180; 424/250; 536/23
[51] Int. Cl.² ........................................ A61K 31/70
[58] Field of Search ........................... 424/250, 180; 260/210 R, 211.5

[56] References Cited
OTHER PUBLICATIONS

Journal of Medicinal Chemistry (1973), vol. 16, No. 2, p. 183.

Terao et al., "Journal of Antibiotics," vol. 13, No. 6 (1960), pp. 401–405.

*Primary Examiner*—V. D. Turner
*Attorney, Agent, or Firm*—Walter Patton; Richard A. Thompson; J. Jerome Behan

[57] ABSTRACT

Emimycin, 1,2-dihydro-1-(2-deoxy-β-D-erythropentofuranosyl)-2-oxypyrazine-4-oxide and the novel compounds 1,2-dihydro-1-(2-deoxy-3,5-di-O-loweralkanoyl-α-D-erythro-pentofuranosyl)-2-oxopyrazine 4-oxide are active anticoccidial agents. Preferably, the alkanoyl group of the novel compounds contain up to six carbon atoms. The compounds are included in compositions useful for the prevention and treatment of coccidiosis in poultry.

4 Claims, No Drawings

METHODS FOR TREATING COCCIDIOSIS WITH EMIMYCIN AND ITS DERIVATIVES

This application is a continuation-in-part of application Ser. No. 449,152 filed March 7, 1974 now abandoned.

SUMMARY OF THE INVENTION

This invention relates generally to the usefulness of emimycin, a pentofuranosyl derivative thereof, 1,2-dihydro-1-(2-deoxy-β-D-erythropentofuranosyl)-2-oxypyrazine-4-oxide and the novel compounds 1,2-dihydro-1-(2-deoxy-3,5-di-O-loweralkanoyl)-α-D-erythro-pentofuranosyl)-2-oxopyrazine 4-oxide for the treatment and prevention of coccidiosis in susceptible animals especially in fowl, and particularly in poultry. In addition, this invention relates to compositions including these compounds as the active ingredient, intimately admixed with an inert carrier for administration to animals infected with coccidia. It is therefore, an object of this invention to provide a method of treatment for coccidiosis using the above compounds. It is also an object of this invention to include these compounds or mixtures thereof in compositions for administration to poultry which compositions are employed to treat coccidiosis. Another object is to provide the novel compounds 1,2-dihydro-1-(2-deoxy-3,5-di-O-loweralkanoyl-α-D-erythro pentofuranosyl)-2-oxopyrazine 4-oxide which are useful in the treatment of coccidiosis. As used herein, the term "treat" includes administration to animals which have developed active symptoms of coccidiosis, as well as animals without overt symptoms, but that have been exposed to causative organisms. Further objects will become apparent upon a further reading of the description.

Coccidiosis is a common and widespread animal disease caused by several species of protozoan parasites of the genus Eimeria. In chickens, implicated species include *E. tenella*, *E. necatrix*, *E. acervulina*, *E. maxima*, *E. hagani*, and *E. brunetti*. *E. tenella* is the causative agent of a severe and often fatal infection of the caeca, which is manifested by severe and extensive hemorrhage, accumulation of blood in the caeca, and the passage of blood in the droppings. *E. acervulina* attacks the small intestine of the chick causing what is known as intestinal coccidiosis. Related species of coccidia such as *E. meleagridis* and *E. adenoides* are causative organisms of coccidiosis in turkeys. When left untreated, the severe forms of coccidiosis lead to poor weight gain, reduced feed efficiency and mortality in fowl. The elimination or control of this disease is, therefore, of paramount importance to the poultry raising industry.

Emimycin and methods for obtaining it are described in Terao, Journal of Antibiotics A13, pp 401-4-5 (1960), Terao, Ibid, A16, pp. 182-6 (1963), Tamura, Bull. Chem. Society, Japan 36, 1187 (1963) and Japanese Patent No. 10,698, 1961. The pentofuranosyl derivative is described in the Journal of Medicinal Chemistry, 16 183 (1973).

Emimycin has the structure:

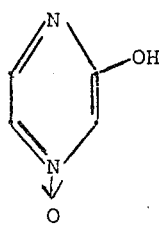

the pentofuranosyl derivative has the structure:

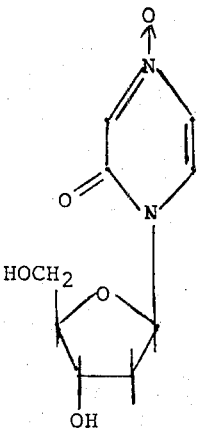

and the loweralkanoyl esters of the derivative have the structure:

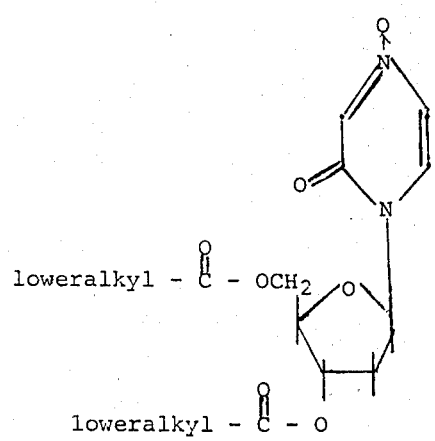

Emimycin and the compounds hereinabove described when used as anticoccidial agents are administered orally as a component of the animal feedstuff in the drinking water, in salt blocks, and in unit dosage forms such as tablets, boluses, or drenches; or parenterally either in solution or in suspension in an aqueous medium. The vehicle in which these anticoccidial agents are distributed is an inert edible carrier or diluent. By an inert edible carrier or diluent is meant one that is nonreactive with respect to these anticoccidial compounds and that may be administered with safety to the animals to be treated. The carrier or diluent is preferably one that is or may be an ingredient of the animal feed.

Thus, the preferred embodiment of this invention are the compositions containing the above emimycin or derivatives or mixtures thereof, which may be successfully employed to treat coccidiosis when administered to animals susceptible to coccidiosis preferably as a component of their feed, although it may also be given dissolved or suspended in the drinking water. According to a preferred aspect of the invention, novel compositions for the treatment of coccidiosis are provided which comprise emimycin or a salt thereof intimately dispersed in or intimately admixed with an inert carrier or diluent.

The compositions which are a preferred feature of this invention are the so-called feed premixes in which an emimycin compound (i.e., emimycin or its pentofuranosyl derivative or the loweralkanoyl esters of said derivative) is present in relatively large amounts and which are suitable for addition to the poultry feed either directly or after an intermediate dilution or blending step. Examples of carriers or diluents suitable for such compositions are animal feed ingredients such as distillers' dried grains, corn meal,, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like. The emimycin compound is intimately dispersed or admixed throughout the solid inert carrier by methods such as grinding, stirring, milling, or tumbling. By selecting proper diluents and by altering the ratio of carrier to active ingredient, compositions of any desired concentration may be prepared. Formulations containing from about 1% to about 40% by weight and preferably from about 2–25% by weight, of an emimycin compound are particularly suitable for addition to poultry feedstuffs. Those having from about 5–20% by weight of coccidiostat are very satisfactory. The active compound is usually dispersed or mixed uniformly in the diluent but in some instances may be sorbed on the carrier. Since it is convenient for the feed manufacturer to use about one pound of feed supplement for each ton of finished feed, the preferred concentration in the supplement is usually a function of the level of active ingredient desired in the finished feed.

For treating poultry, the feed supplement is uniformly dispersed in the animal feed by suitable mixing or blending procedures.

Usually the feed supplements are further diluted with materials such as corn meal or soybean meal before being incorporated in the animal feed. In this intermediate processing step, the level of the emimycin compound in the carrier is brought down to about 0.1 to 1.0% by weight. This dilution serves to facilitate uniform distribution of the coccidiostat in the finished feed. The finished feed is one that contains a source of fat, protein, carbohydrate, minerals, vitamins and other nutritional factors.

Very low levels of an emimycin compound in an animal fed are sufficient to afford good protection against coccidiosis in a susceptible animal. Suitable amounts range from 0.003% to about 0.1% by weight in the feed. Preferably, the compound is administered in an amount equal to about 0.003 to 0.025% by weight of the feed. Optimum results are obtained by feeding at a level of about 0.006 to 0.0125% by weight of the finished feed. For therapeutic treatment of an established coccidial infection, higher amounts of an emimycin compound, i.e., up to about 0.01% by weight of the feed consumed, can be employed. The most advantageous dosage level will, of course, vary somewhat with particular circumstances such as the type and severity of the coccidial infection to be treated.

The above concentrations are described on the basis of crystalline material, that is, material which is substantially pure. It is to be understood that an equivalent amount of emimycin activity can be obtained by employing less pure material derived from various stages of emimycin fermentation including whole culture, or filtered beer. For example, the filtered beer can without further purification be spray dried directly into the inert carrier. When employing such a source of emimycin activity, the material used is advisably assayed and the quantity employed be factored so it is equivalent to the above referred to concentrations.

In the above discussion of this invention, emphasis has been placed on solid compositions wherein the active ingredient is mixed with an edible carrier in a feed supplement, in a so-called premix or in the final feedstuff. This is the preferred method of administering the emimycin compound. An alternate method of treatment is to dissolve or suspend the emimycin compound in the drinking water of the animals.

This invention is not limited to anticoccidial compositions having emimycin compounds as the sole active ingredient. Also contemplated within its scope is what might be called "combined treatment" where a emimycin compound and one or more other anticoccidials are administered concurrently. For such purposes, compositions may be prepared containing a emimycin compound admixed with one or more other coccidiostats such as sulfaquinoxaline, other sulfa compounds, 4,4'-dinitrocarbanilide-2-hydroxy-4,6-dimethylpyrimidine complex, 3,3'-dintrodiphenyldisulfide, 5-nitrofurfural semicarbazone, amprolium, zoalene, buquinolate, ethopabate, monensin and the like.

It will likewise be understood by those skilled in this art that special feed supplement formulations and finished animal feeds contaning vitamins, antibiotics, growth-promoting agents and other nutritional substances may include an emimycin compound of this invention. A feed supplement of this type is the following:

| Ingredient: | Amount/lb. of Supplement, grams |
|---|---|
| Riboflavin | 0.64 |
| DL-calcium pantothenate | 2.10 |
| Niacin | 3.67 |
| Choline chloride | 50.00 |
| Vitamin B$_{12}$ concentrate | 1.30 mg. |
| Procaine penicilline | 0.84 |
| Vitamin A (100,000 u./g.) | 3.38 |
| Vitamin D$_3$ (200,000 u./g.) | 0.68 |
| Arsanilic acid | 18.36 |
| Butylated hydroxy toluene | 23.15 |
| DL-methionine | 23.15 |
| Emimycin | 23.00 |
| Distillers' grains to 1 pound. | |

Animal feed premixes having the following compositions are prepared by intimately mixing the emimycin compound and the particular edible solid diluent or diluents:

| | lbs. |
|---|---|
| A. Emimycin | 12.5 |
| Distillers' dried grains | 87.5 |
| B. Emimycin | 15.0 |
| Soya mill feed | 45.0 |
| Fine soya grits | 40.0 |
| C. Emimycin | 5.0 |
| Molasses solubles | 95.0 |
| D. Emimycin | 15.0 |
| Corn distillers' grains | 55.0 |

| | lbs. |
|---|---|
| Corn germ meal | 30.0 |

These supplements and premixes are made by mechanical milling or mixing of the ingredients to insure uniform distribution of the active compound and are then added to feed in such an amount that the concentration of emimycin or its salt is as hereinbefore specified.

The following example is presented in order to illustrate this invention and should not be construed as limitative of the invention.

Three 11-day old female white leghorns weighing between 75 to 90 gm. each were maintained on a vitamin supplemented diet (Pennfield 190) containing the sample to be tested. One day later, each chicken was orally inoculated with $4 \times 10^5$ sporulated oocysts of $E.$ $acervulina$ and maintained on the same diet for five more days. Weights of each of the birds were recorded on days 1, 3, 5, 6 and 7 during the assay; the rate of weight gains during days 1 to 5 ($B_1$) was a parameter of drug toxicity, whereas growth rate from day 5 to day 7 reflected the $E.$ $acervulina$ infection. Serum was collected from each chicken through cardiac puncture on the final day of the assay. The serum albumin level was measured and used as another indicator of coccidial infection. The internal duodenal lesions of each chicken was also examined and the scores were the third parameter of $E.$ $acervulina$ infection. All the data were then pooled together to produce an anti-$E.$ $acervulina$ index as the final judgment of the extent of infection. The formula to calculate the index is as follows:

$B_2/B_1 \times 100 + \%$ normal serum albumin-lesion score $\times 10$

The results are set forth in the following table:

Preparation of 1,2-Dihydro-1-(2-deoxy-3,5-di-O-acetyl-α-D-erythro-pentofuranosyl)-2-oxopyrazine 4-oxide A solution of 200 mg of 1,2-dihydro-1-(2deoxy-β-D-erythro-pentofuranosyl)-2-oxopyrazine 4-oxide (Berkowitz et al., Journal of Medicinal Chemistry, 1973, Volume 16, No. 2., pages 183–184) in 4 ml. of pyridine was treated at room temperature with 0.2 ml. of acetic anhydride. After standing overnight, the reaction mixture was treated in the cold with water, extracted into methylene chloride and washed with dilute HCl and 5% $NaHCO_3$. Removal of the dried solvent left the diacetate which was purified by column chromatography on silica gel.

In a similar manner other lower alkanoyl esters may be prepared using the corresponding alkanoyl halide or anhydride.

The above compound as well as the unesterified pentofuranosyl derivative can be utilized in the same manner as the Emimycin in the preparations given above.

Many other equivalent modifications will be apparent to those skilled in the art from a reading of the foregoing without a departure from the inventive concept.

What is claimed is:

1. A method for treating coccidiosis in poultry which comprises orally administering to poultry an anticoccidially effective amount of a compound selected from the group consisting of emimycin, 1,2-dihydro-1-(2-deoxy-β-D-erythropentofuranosyl)-2-oxypyrazine-4-oxide and 1,2-Dihydro-1-(2-deoxy-3,5-di-O-loweralkanoyl-α-D-erythropentofuranosyl)-2-oxopyrazine 4-oxide.

2. The method according to claim 1 in which said compound is admixed with an inert carrier in the amount of 0.003 to 0.1% by weight.

3. The method according to claim 1 in which said compound is admixed with an inert carrier in the amount from 0.006 to 0.0125% by weight.

4. An anticoccidial premix composition which comprises a carrier and in the amount of 2 to 25% by weight of the composition an anticoccidial agent which is 1,2-dihydro-1-(2-deoxy-3,5-di-O-loweralkanoyl-α-D-erythro-pentofuranosyl)-2-oxopyrazine-4 oxide.

* * * * *

| | Activities of Emimycin Against $E.$ $acervulina$ | | | | | |
|---|---|---|---|---|---|---|
| Doses (%) | $B_1$* | $B_2$* | Serum Albumin (% Normal) | Lesion Scores | Anti-$E.$ $acer.$ Index | Evaluation |
| 0.1000 | 5.92 | 9.67 | 126.7 | 0.0 | 290.1 | Active and Good Weight Gain |
| 0.1000 | 3.50 | 10.83 | 104.1 | 0.0 | 406.9 | Active and Fair Weight Gain |
| 0.0500 | 7.92 | 6.84 | 95.9 | 0.0 | 182.2 | Active and Good Weight Gain |
| 0.0250 | 7.75 | 6.50 | 82.2 | 0.0 | 166.1 | Active and Good Weight Gain |
| 0.0125 | 7.58 | 6.17 | 84.2 | 4.0 | 125.5 | Moderately Active and Good Weight Gain |

*Weight gains in gm./bird/day.